United States Patent [19]

Buckland et al.

[11] Patent Number: 5,382,682
[45] Date of Patent: Jan. 17, 1995

[54] NITROANILIDES AND THEIR PREPARATION

[75] Inventors: Paul R. Buckland, Pittsford; Lee H. Latimer, Rochester, both of N.Y.

[73] Assignee: Eastman Kodak Company, Rochester, N.Y.

[21] Appl. No.: 920,573

[22] PCT Filed: Dec. 16, 1991

[86] PCT No.: PCT/EP91/02417

§ 371 Date: Aug. 18, 1982

§ 102(e) Date: Aug. 18, 1992

[87] PCT Pub. No.: WO92/11230

PCT Pub. Date: Jul. 9, 1992

[30] Foreign Application Priority Data

Dec. 18, 1990 [GB] United Kingdom ........... 9027428

[51] Int. Cl.[6] ............... C07C 233/15; C07C 233/66
[52] U.S. Cl. ............................. 564/184; 564/221
[58] Field of Search ............... 564/162, 192, 179, 184, 564/221

[56] References Cited

U.S. PATENT DOCUMENTS 3,798,258  3/1974  Patchett et al. ............ 564/179
5,107,022  4/1992  de Besset .................... 564/192

OTHER PUBLICATIONS

Journal Of The Chemical Society. 1957, Letchworth GB, pp. 295-301; A. R. Fox: 'Oxidations With Phenyl Iodosoacetate. Part VI.' cited in the application, see p. 299.

Journal Of Medicinal Chemistry. vol. 20, No. 6, 1977, Washington US pp. 826-829; H. Singh: 'Systhesis Of 5-Chloro-3-'Nitro-4'-Substituted Salicylanilides, A New Series Of Anthelmintic And Antimicrobial Agents' see p. 827.

Pharmazie, vol. 45, No. 1, Jan. 1990, Berlin D. D. pp. 34-37; R. P. Srivastava et al: 'Synthesis Of 2,5-Distributed Benzimidazoles<1,3,4–Thiadiazoles And 3,5-Diiodosalicylanilides As Structural Congeners Of Rafoxanide And Closantel' see table 2.

Chemical Abstracts, vol. 57, No. 6, 17 Sep. 1962, Columbus, Ohio, US; abstract No. 7270G, col. 7270; see abstract & CAN. J. Chem. vol. 40, 1062, pp. 165-169; G. Frangatos: 'The Synthesis Of Some Basic Diphenyl Ethers'.

Anales de Fisica y Quimica (1966), p. 451, P. E. Verkade and C. P. Van Dijk Abstract.

*Primary Examiner*—Richard L. Raymond
*Assistant Examiner*—B. Bembenick
*Attorney, Agent, or Firm*—Arthur E. Kluegel

[57] ABSTRACT

Novel aryloxy-nitroanilides of formula

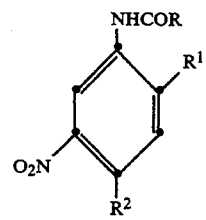

wherein R is alkyl from 1 to 5 carbon atoms or unsubstituted or substituted aryl of from 6 to 10 carbon atoms; one of $R^1$ and $R^2$ is a hydrogen atom and the other is aryloxy, wherein the aryl is unsubstituted or substituted with one or more alkyl of from 1 to 10 carbon atoms, with the proviso that when R is methyl, $R^1$ may not be unsubstituted phenoxy and when R is 2-hydroxy-5-chlorophenyl, $R^2$ may not be unsubstituted or chloro or methyl substituted phenoxy, and a method of preparing them. The compounds are suitable as intermediates for the preparation of anilines, required in the preparation of useful photographic and pharmaceutical compounds.

3 Claims, No Drawings

NITROANILIDES AND THEIR PREPARATION

This invention relates to novel aryloxy-nitroanilides and a process for preparing them.

Certain nitroanilides are suitable as intermediates which can be readily converted to their corresponding anilines, required in the preparation of useful photographic and pharmaceutical compounds. Previous methods of preparation have not been suitable for large scale synthesis of anilines particularly for those analogues which are ballasted. Selective reduction of dinitro analogues as in Anales de Fisica y Quimica (1966), 451, P. E. Verkade and C. P. Van Dijk result in the formation of mixtures of isomers with consequent separation difficulties, whilst preparation of the required anilines from ethyl-4-chloro-3-nitrobenzoate is a protracted and expensive procedure.

A method of preparing 2-phenoxy-5-nitrotroacetanilide in low yield is already known (A. R. Fox and K. H. Pausacker, J Chem Soc. (1957), 295–301) in which 2-chloro-5-nitroacetanilide is reacted with a large excess of sodium phenoxide under molten conditions and in the presence of copper powder.

The present invention relates to a method of preparing aryloxy-nitroanilides which avoids this use of a large excess of phenol, is suitable for large scale synthesis end gives the anilides in good yields, and to the novel intermediates thereof. The anilides can be subsequently hydrolysed to the required anilines using known methods.

According to the present invention there are provided novel intermediates of formula (I).

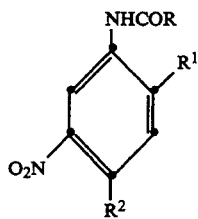

wherein R is alkyl from 1 to 5 carbon atoms or unsubstituted or substituted aryl of from 6 to 10 atoms, one of $R^1$ and $R^2$ is hydrogen and the other is aryloxy, wherein the aryl is unsubstituted or substituted with one or more alkyl of from 1 to 10 carbon atoms, with the proviso that when R is methyl, $R^1$ may not be unsubstituted phenoxy and when R is 2-hydroxy-5-chlorophenyl, $R^2$ may not be unsubstituted or chloro or methyl substituted phenoxy.

As used herein and throughout the specification the term alkyl denotes a straight or branched chain alkyl group.

When R is a substituted aryl group, it may be substituted, for example, by one or more halo, alkyl, ester or sulfonyl-containing groups. However, preferred intermediates are those wherein R is a phenyl group or most preferably a methyl group and especially those wherein one of $R^1$ and $R^2$ is a substituted phenoxy group. Particularly preferred compounds are
2-(4-t-octylphenoxy)-5-nitroacetanilide,
4-(4-t-octylphenoxy)-3-nitroacetanilide,
2'-(2,4-di-t-pentylphenoxy)-5'-nitrobenzanilide, and
2-(4-t-butylphenoxy)-5-nitrobenzanilide and
2-phenoxy-5-nitrobenzanilide.

In a further aspect of the present invention there is provided a method of preparing intermediates of formula (I)'

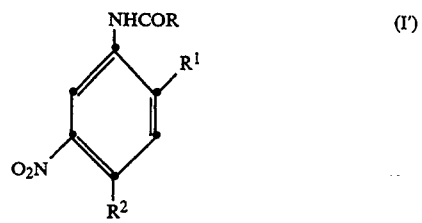

wherein R is alkyl from 1 to 5 carbon atoms or unsubstituted or substituted aryl of from 6 to 10 carbon atoms, one of $R^1$ and $R^2$ is hydrogen and the other is an aryloxy, wherein the aryl is unsubstituted or substituted with one or more alkyl of from 1 to 10 carbon atoms, comprising the step of reacting a compound of formula (II)

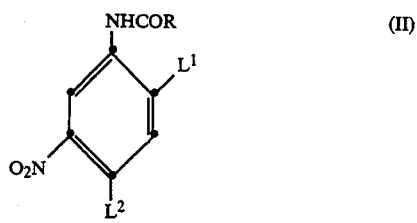

wherein R is as defined above and one of $L^1$ and $L^2$ is a hydrogen and the other is a leaving group, with a compound of formula $R^3$ OH, wherein $R^3$ is aryl as defined for $R^1$ and $R^2$.

Preferably the reaction is carried out in the presence of a base, such as potassium carbonate or sodium hydride, and with a polar aprotic solvent, such as dimethylformamide or diglyme (bis-(2-methoxyethyl) ether, or a nonpolar hydrocarbon solvent, such as xylene. Although the most preferred solvent is dimethylformamide these other solvents work well at elevated temperatures, especially at their boiling points.

The leaving group is preferably a halogen atom, especially chloro or fluoro, or a sulphonate group.

The most suitable reaction temperature will vary according to the reactants involved and in particular the leaving group. When R is methyl and the leaving group is chloro, temperatures in excess of 140° C. are advantageous, whilst the corresponding fluoro compound reacts more effectively at between room temperature to 100° C. When R is phenyl, use of room temperature minimises the formation of by-products.

An extension of the method of the invention is that 2-fluoro-5-nitroaniline can also react at elevated temperatures with a compound $R^3$OH, preferably under basic conditions and with a polar aprotic solvent to give 2-aryloxy-5-nitroanilines.

The invention is illustrated by the following examples:

EXAMPLE 1

2-(4-t-Octylphenoxy)-5-nitroacetanilide [R=Me; $R^1$=4-t-octylphenoxy; $R^2$=H]

A mixture of 2-chloro-5-nitroacetanilide (214 g, 1.0 mole), 4-t-octylphenol (227 g, 1.1. mole), finely ground anhydrous potassium carbonate (207 g, 1.5 mole) and dimethylformamide (300 ml) was heated and stirring begun when the mixture became sufficiently mobile at 60° C. At 140° C. an exotherm to 150° C. occurred and vigorous evolution of carbon dioxide commenced. The mixture was stirred at 150° C. for a further 1.5 hours, after which time a t.l.c. showed very little starting material. After cooling to 110° C., toluene (600 ml) was added and the mixture washed with hot (50° C.) water (750 ml). The aqueous layer was run off and the toluene removed to give a dark red oil to which methanol (1000 ml) was added. After cooling to 0° C., the solid was collected, washed with ice cold methanol (4×100 ml) and dried to give the product (210 g). Partial evaporation of the liqours and cooling gave a second crop of product which was collected, washed with methanol (3×50 ml), dried and combined with the first crop to give a total yield of 262 g (68%). An analytically pure sample of the product melted at 140° C.

EXAMPLE 2

4-(4-t-Octylphenoxy)-3-nitroacetanilide [R=Me; R=H $R^2$=4-t-octylphenoxy]

Using conditions similar to the above (reaction time, 3.5 hours), 4-chloro-3-nitroacetanilide was reacted with 4-t-octylphenol to give after column chromatography (2:1 petrol:ethyl acetate) the product 27.0 g (70%) as a pale orange solid m.p 121° C.

EXAMPLE 3

2'-(2,4-di-t-pentylphenoxy)-5'-nitrobenzanilide [R=Ph $R^1$=2,4-di-t-pentylphenoxy; $R^2$=H].

2,4-di-t-pentylphenol (3.25 g, 13.9 mmole) was slowly added to 80% sodium hydride (0.42, 14 mmole) in dry dimethylformamide (10 ml). After hydrogen evolution had ceased, solid 2-fluoro-5-nitrobenzanilide (3.2 g, 12.3 mmole) was added and the deep red reaction mixture stirred at room temperature for four days. The mixture was poured into water and extracted with ethyl acetate. The combined organic extracts were washed successively with water and saturated sodium bicarbonate solution and then dried over sodium sulphate. Removal of the solvent gave an oil which on crystallization from n-hexane gave the product as a solid 3.84 g (70%) m.p 123° C.

EXAMPLE 4

2-(4-t-butylphenoxy)-5-nitrobenzanilide [R =Ph; $R^1$=4-t-butylphenoxy; $R^2$=H]

To 0.18 g (6 mmole) of 80% sodium hydride in 7.5 ml of dry dimethylformamide was slowly added 0.9 g (6 mmole) of 4-t-butylphenol in 2.5 ml of dimethylformamide. After cessation of hydrogen evolution, 1.3 g (5 mmole) of solid 2-fluoro-5-nitrobenzanilide was added and the deep red solution was stirred at room temperature for 5 days. The reaction mixture was diluted with water and extracted with ethyl acetate. The organic layer was washed with IN hydrochloric acid, saturated aqueous sodium bicarbonate solution, dried with magnesium sulphate and the solvent removed to yield the crude product. Recrystallisation from methylene chloride and hexare yielded 0.92 g product (47%) m.p. 138°–140° C.

EXAMPLE 5

2-phenoxy-5-nitrobenzanilide [R =Ph; $R^1$=phenoxy; $R^2$=H]

The procedure of Example 4 was followed giving a good yield of product which was characterised by its n.m.r. spectrum.

We claim:
1. 2-(4-t-Octylphenoxy)-5-nitroacetanilide.
2. 4-(4-t-Octylphenoxy)-3-nitroacetanilide.
3. 2'-(2,4-di-t-pentylphenoxy)-5'-nitrobenzanilide.

* * * * *